United States Patent [19]

Penza et al.

[11] Patent Number: 5,527,546
[45] Date of Patent: Jun. 18, 1996

[54] HUMAN INTERLEUKIN 6 INHIBITOR

[75] Inventors: Delia E. Penza, Alamo; Susan K. Faris, San Francisco; Kenneth J. Lembach, Danville, all of Calif.

[73] Assignee: Bayer Corporation, Berkeley, Calif.

[21] Appl. No.: 288,516

[22] Filed: Aug. 10, 1994

[51] Int. Cl.$^6$ ................................................. A61K 35/12
[52] U.S. Cl. ................................................. 424/573
[58] Field of Search ..................................... 424/573

[56] References Cited

PUBLICATIONS

Twigg et al., J. Lab Clin Med. 124(2):283–292 (1994).

*Primary Examiner*—Michael G. Wityshyn
*Assistant Examiner*—Jean C. Witz
*Attorney, Agent, or Firm*—James A. Giblin

[57] ABSTRACT

A previously undescribed Interleukin-6 inhibitor activity has been successfully isolated from the supernatant of the human promyelocytic leukemia cell line HL-60. Treatment of the HL-60 cell line with cycloheximide prevents the appearance of the inhibitory activity in the cellular supernatant. Incubation of the HL-60 supernatant with trypsin destroys the activity. The above observations indicate the inhibitor is a protein. Membrane and gel filtration studies indicate the protein has a molecular weight between 10,000 and 30,000 daltons. The inhibitor was partially isolated from other proteins by dye-ligand and reverse phase chromatography.

11 Claims, 7 Drawing Sheets

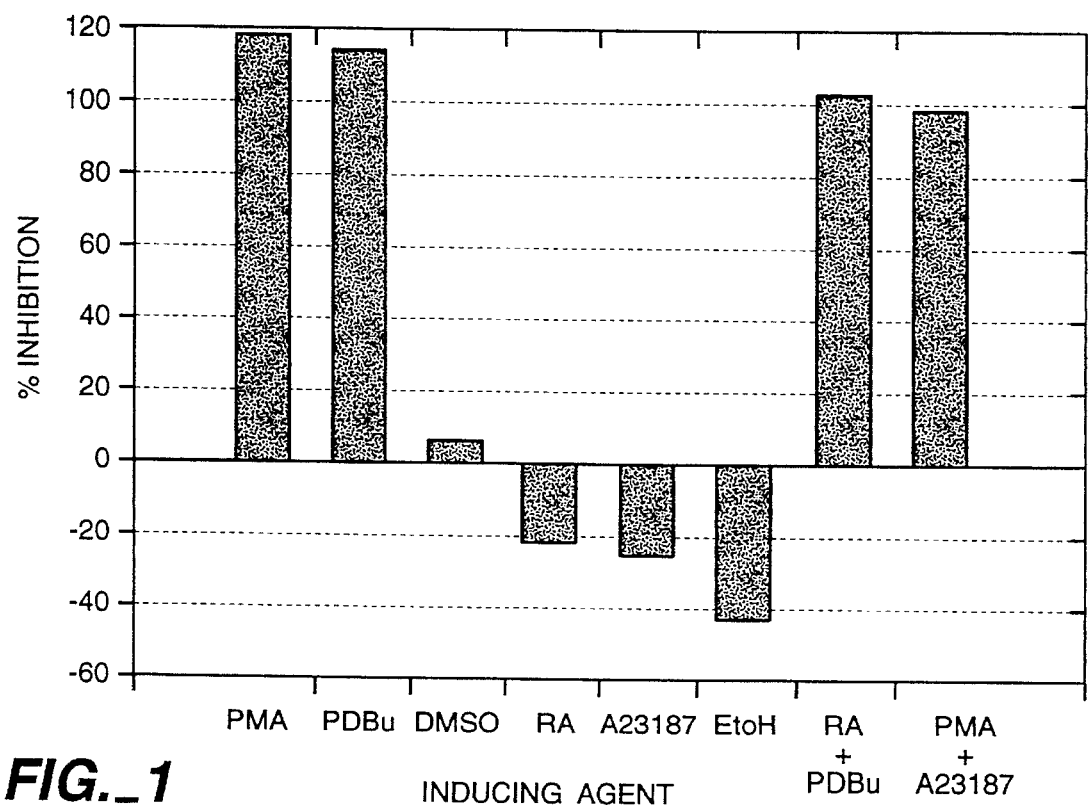
FIG._1
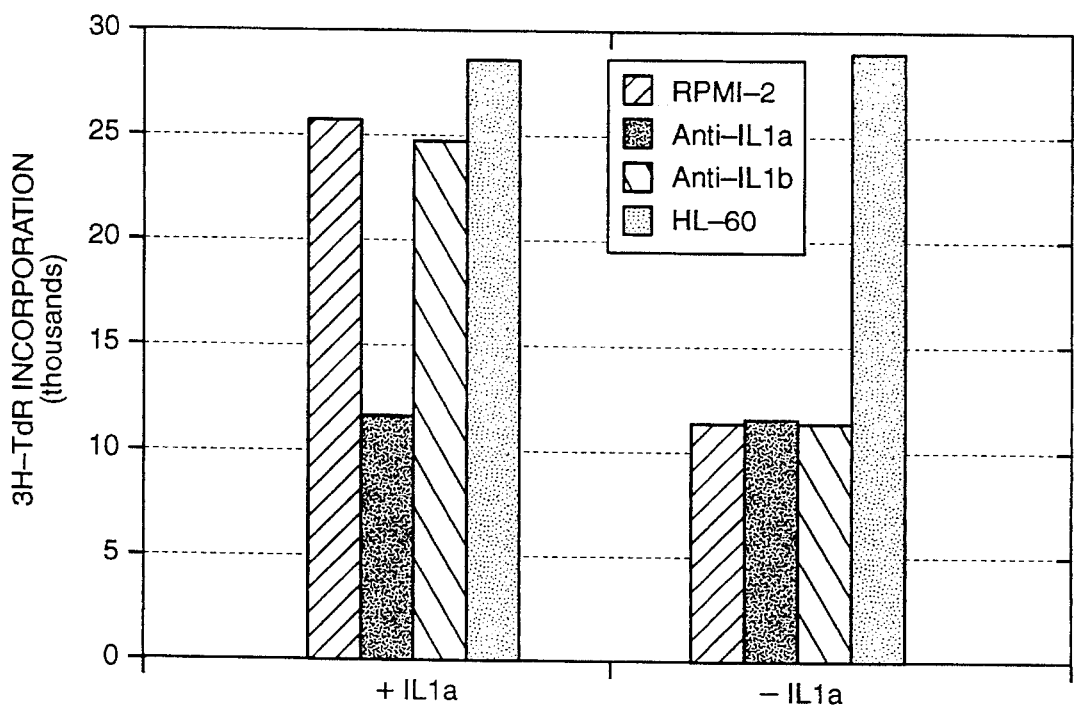
FIG._2

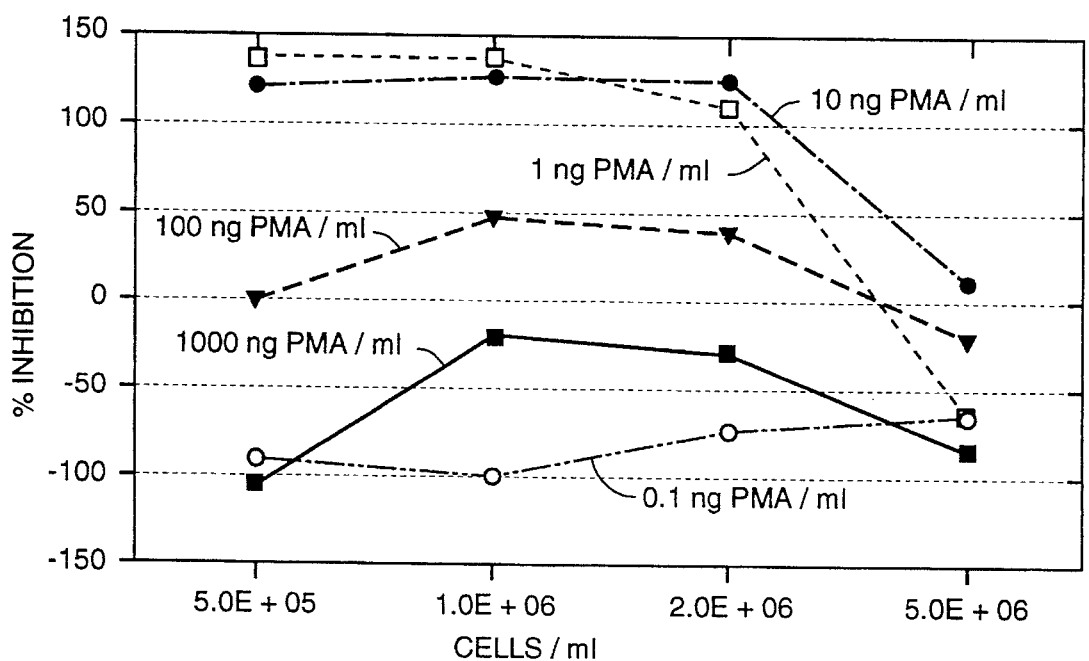
FIG._3A
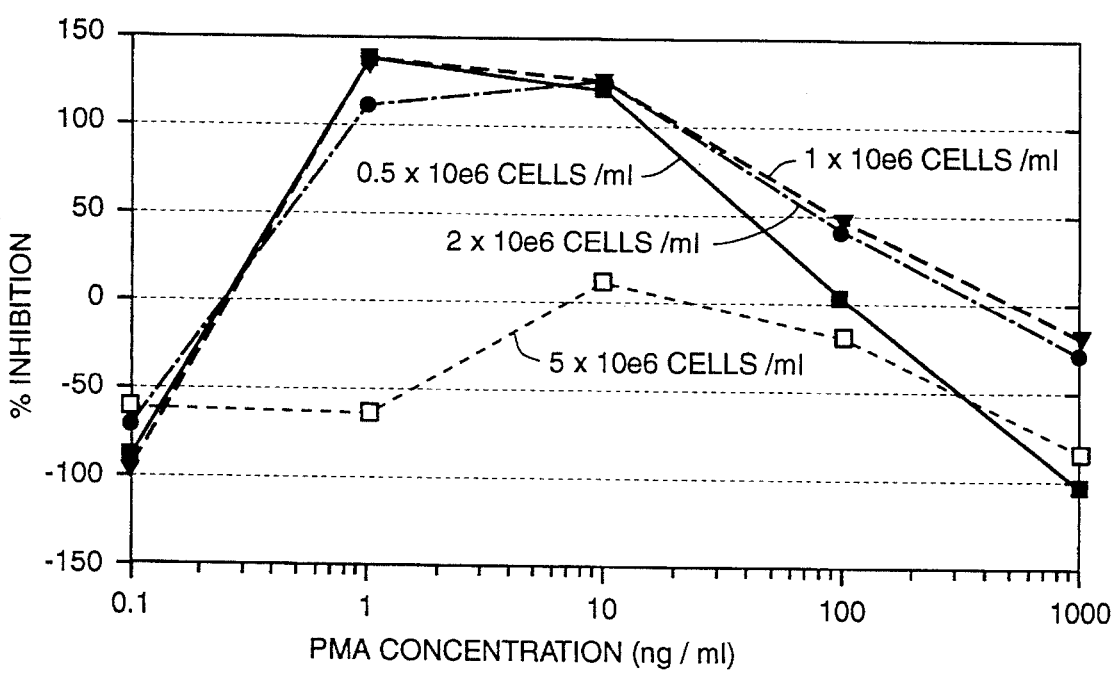
FIG._3B

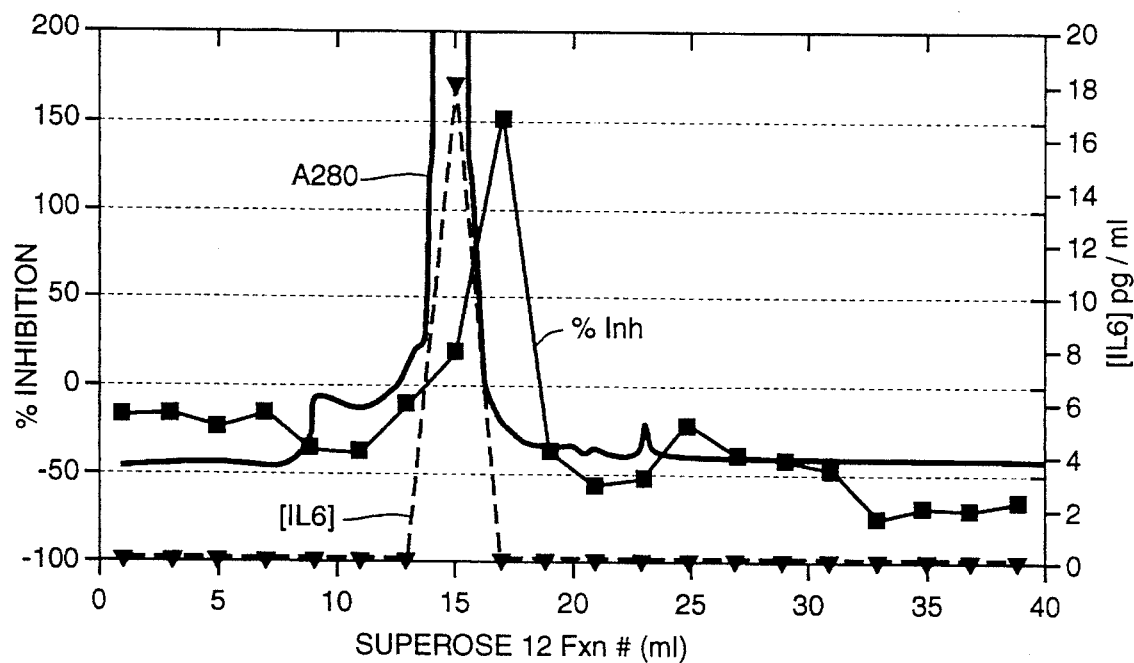
FIG._4
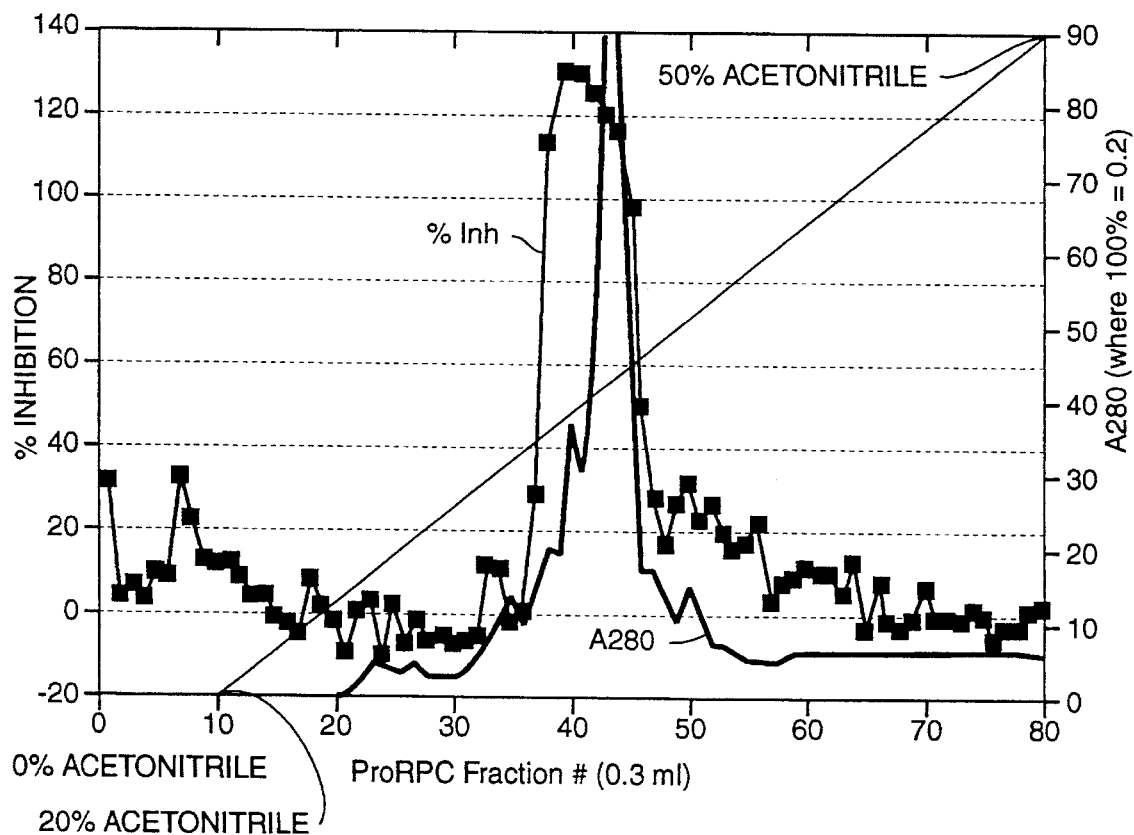
FIG._8

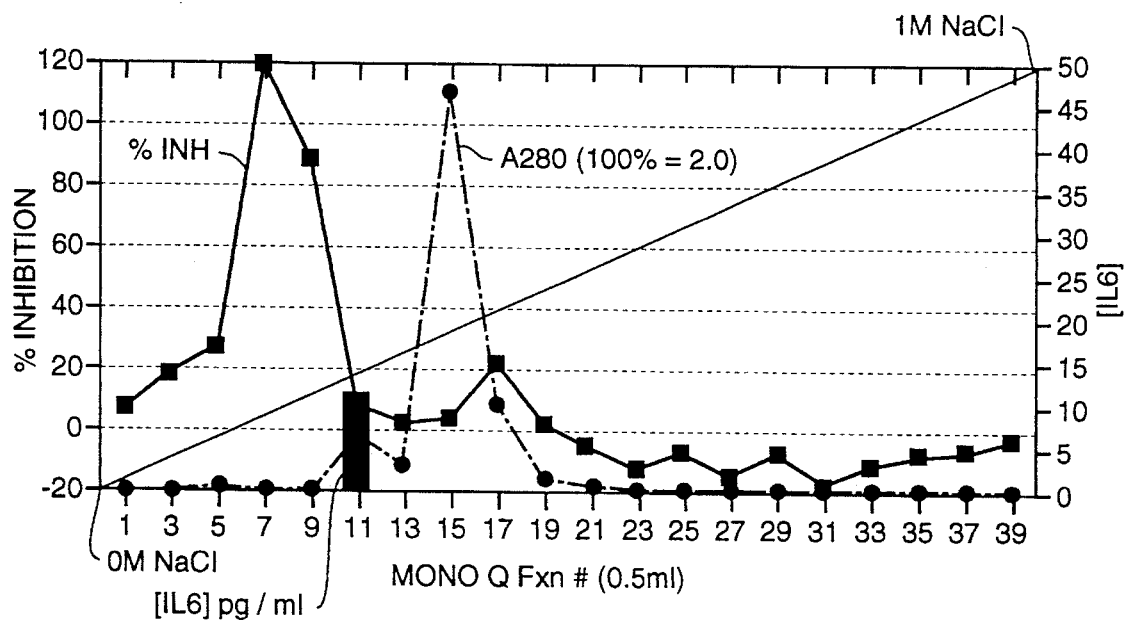
FIG._5
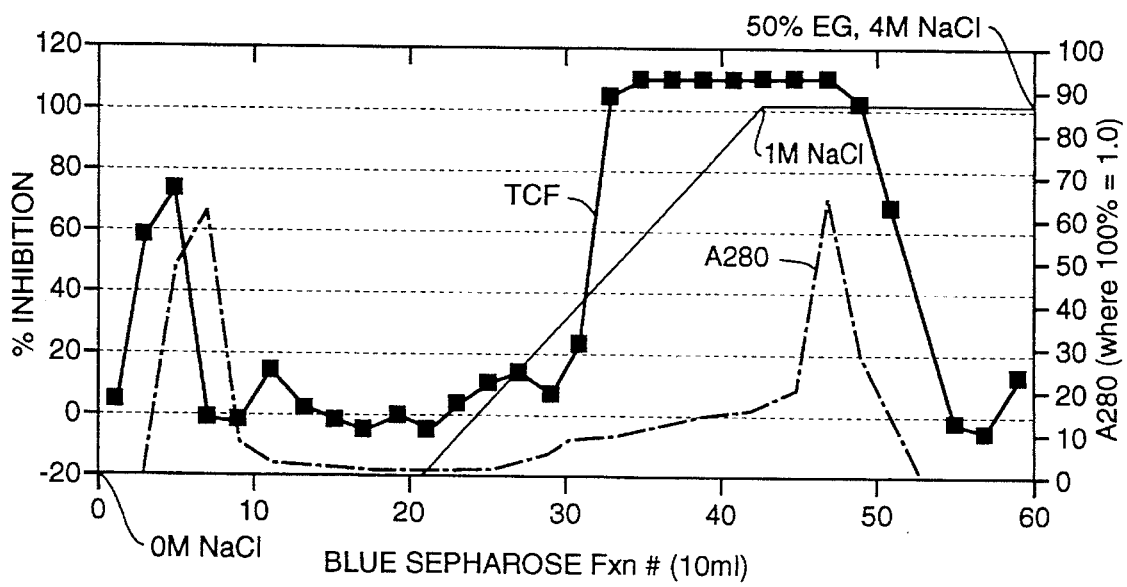
FIG._6

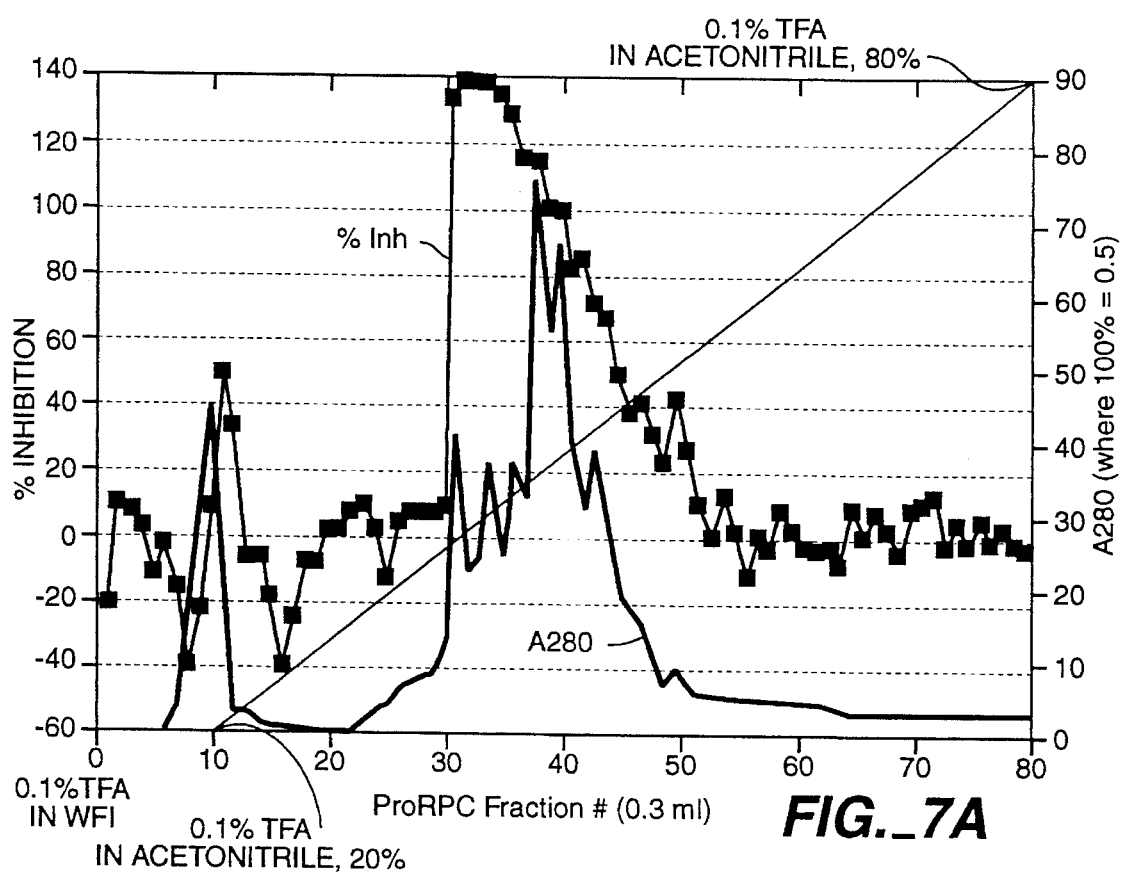
FIG._7A
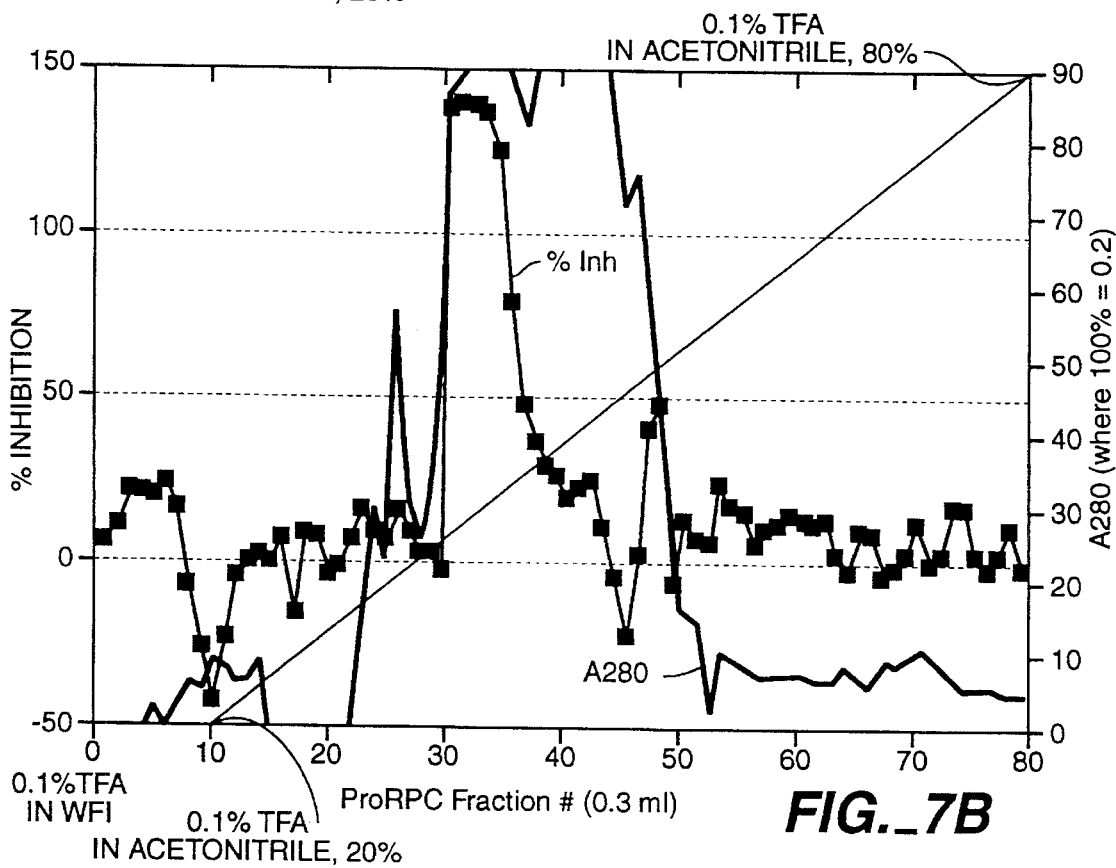
FIG._7B

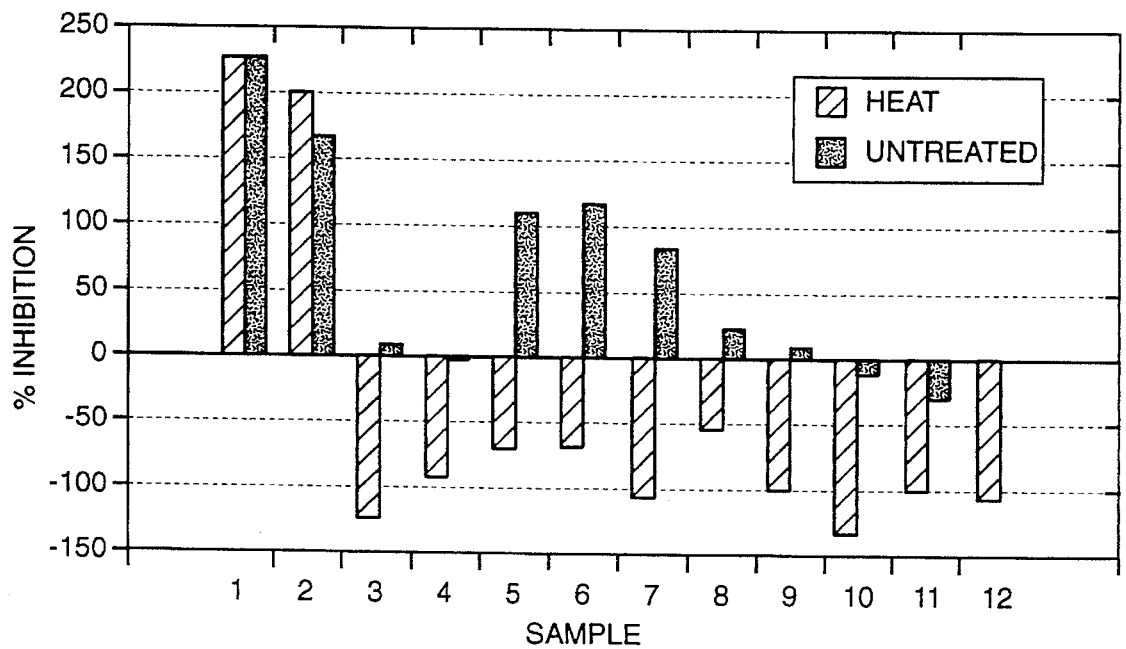
FIG._9
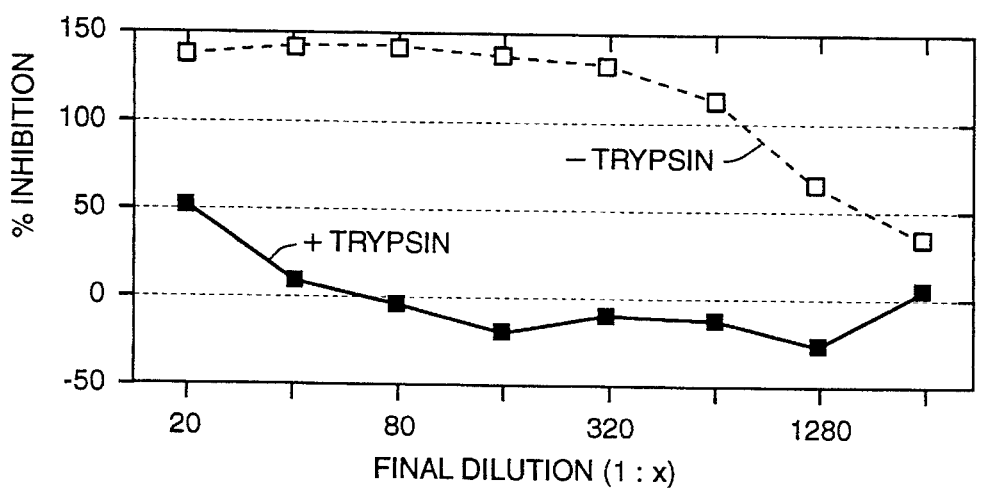
FIG._10

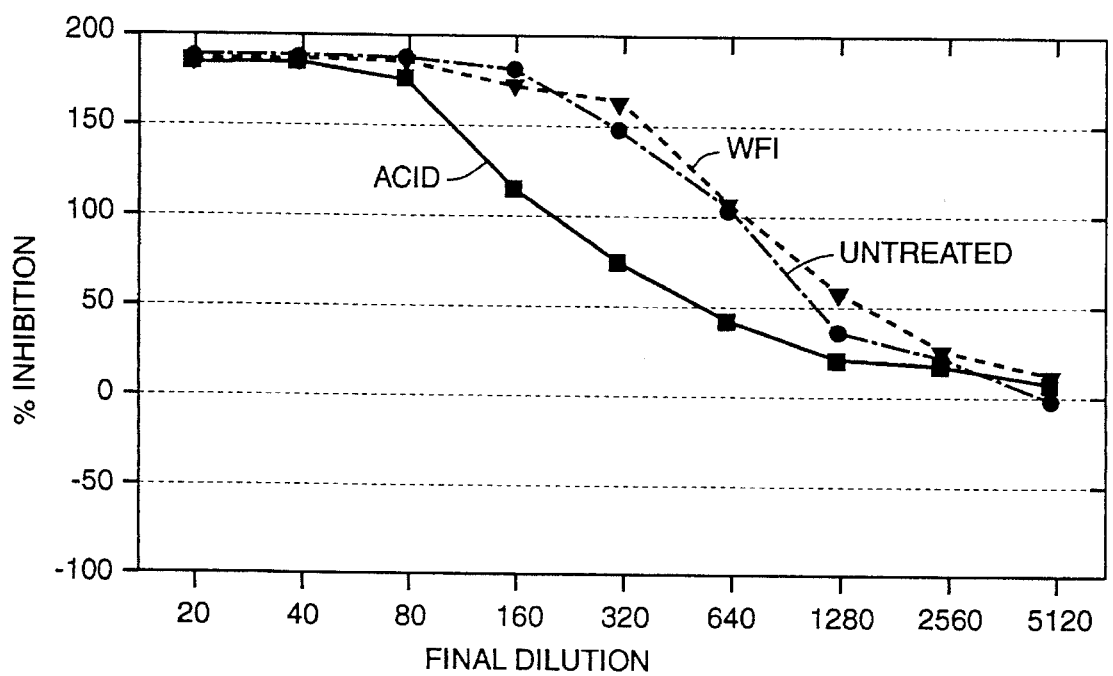
FIG._11
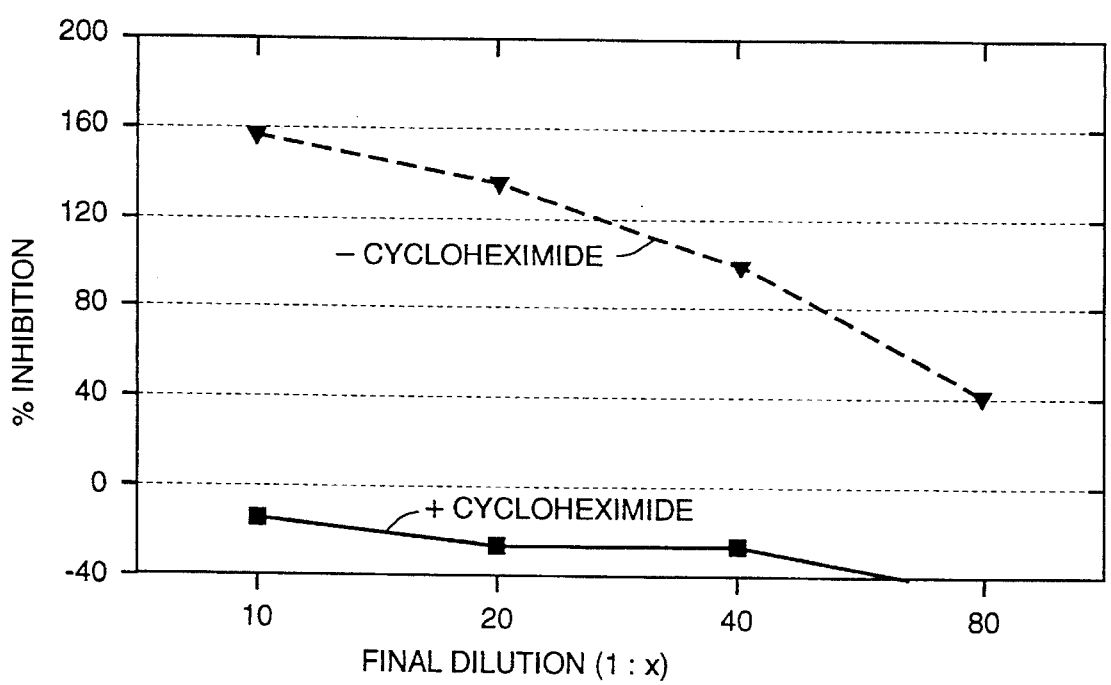
FIG._12

HUMAN INTERLEUKIN 6 INHIBITOR

BACKGROUND OF THE INVENTION

1. Field

This disclosure is concerned generally with a novel cytokine antagonist preparation and specifically with the preparation, characterization, and use of an Interleukin-6 inhibitor which can be isolated from tissue culture fluid and has been found to have in vitro Interleukin-6 antagonist activity.

2. Background

The involvement of Interleukin-6 (IL-6) in human health and disease is under intensive investigation. Elevated levels of IL-6 have been found in the bloodstream and/or body fluids of individuals with bacterial and viral infections, trauma, autoimmune disorders, and neoplasias. Correlations of IL-6 levels with severity of symptoms and the beneficial effect of anti-IL-6 antibodies in animal models suggest that the cytokine may play a pathophysiological role in some disease indications. Antagonists of IL-6 may therefore be of therapeutic use.

A specific, natural IL-6 antagonist has yet to be described. Portier et al. (*Blood*, 81(11):3076–82 (1993)) found that γ-interferon (γ-IFN) will inhibit IL-6 dependent myeloma cell growth but γ-IFN does not inhibit IL-6 activity in other types of in vitro assays.

Brakenhoff et al. (*J. Biol. Chem.*, 269(1):86–93 (1994)) engineered biologically inactive IL-6 mutants which bound to the 80 kD IL-6R but did not bind to gp130, thus preventing signal transduction. These mutant proteins acted as IL-6 antagonists by preventing native IL-6 from binding to the IL-6 receptor subunits. However, the mutant protein's potential immunogenicity could be a difficulty for therapeutic use.

Klein et al. (*Blood*, 78:1198–1204 (1991)) found that administration of a murine anti-IL-6 antibody to a patient with leukemia blocked myeloma cell proliferation in the bone marrow. Again though, because the murine antibody is a foreign protein, there is the potential for immunogenicity.

It has been postulated that bioengineered derivatives of a soluble 80 kD receptor would act as an IL-6 antagonist by binding to circulating IL-6 but not to gp130 thus preventing signal transduction (J. Bauer, *Biotechnology Therapeutics*, 2(3&4):285–298 (1991)). However, these proteins might have an epitope that could be recognized as foreign and could still be immunogenic if used as a therapeutic. Bauer also stated that clinical trials using human anti-human IL-6 antibodies for the treatment of multiple myelomas have begun (Id.). At this time, the outcome of the clinical trials is unknown.

Monocytes/macrophages have been shown to produce both cytokines and cytokine inhibitors, such as the IL-1 inhibitor Roberts et al. found in Respiratory Syncytial Virus (RSV) infected monocytes (*J. Exp. Med.*, 163:511–519 (1986)) and the IL-1 receptor antagonist protein (Janson et al., *J. Immunol.*, 147(12):4218–4223 (1991)). In this invention, we investigated the possibility that such cells may also secrete an IL-6 inhibitor. Since it was difficult to establish a consistent supply of human peripheral blood monocytes, we utilized the human promyelocytic leukemia cell line, HL-60. Treatment of HL-60 with phorbol diesters induces differentiation to cells exhibiting several characteristics of macrophages (Hall et al., *Cell. Immunol.*, 76:58–68 (1983)), while dimethyl sulfoxide (DMSO) or retinoic acid (RA) treatment results in differentiation along the granulocytic pathway (Leftwich et al., *Canc. Res.*, 46:3789–3792)). We found that exposure of HL-60 cells to phorbol diesters specifically induced secretion of an IL-6 inhibitor. It appears that this IL-6 inhibitor is an apparently novel human protein. Because the HL-60 cell line is human, the IL-6 inhibitor should contain the human amino acid sequence and therefore not be immunogenic in vivo. This would be an improvement over the prior examples of IL-6 antagonists.

SUMMARY OF THE INVENTION

The inhibitor preparation of this disclosure comprises an inhibitor characterized by being obtainable from the HL-60 cell line and having a molecular weight between about 10,000 and 30,000 daltons as determined by gel filtration chromatography. The inhibitor is also bindable and elutible from Blue Sepharose®, bindable and elutible from anion exchange resins and bindable and elutible from reverse phase chromatography resins. The inhibitor suppresses the IL-6-dependent proliferation of the B9 cell line. The inhibitory activity is reduced greater than 50 fold by trypsin digestion, and treatment of the HL-60 cell line with cycloheximide during stimulation completely abrogates the inhibitory activity of the cell supernatant. The activity is resistant to acid and heat treatment.

The inhibitor may be partially isolated from stimulated HL-60 supernatants by chromatography on Blue Sepharose®, anion exchange chromatography, and reverse phase chromatography.

The inhibitor has been found useful in studying the effect of IL-6 on cellular functions in vitro and may in time be found to be therapeutically useful in treating disorders characterized by increased IL-6 levels.

DESCRIPTION OF THE FIGURES

FIG. 1: Induction of IL-6 Inhibitor in HL-60 Cells

HL-60 cultures were treated with PMA (10 ng/mL), PDBu (130 ng/mL), A23187 (50 ng/mL), DMSO (1.2% v/v), PMA and A23187, or ethanol (EtOH, 1% v/v) for 24 hours. RA (10 nM) was added 5 days prior to 24 hour induction with or without PDBu (130 ng/mL). Cells were washed and resuspended in RPMI-2 at $1\times10^6$ cells/mL. After 3 days incubation, cell-free culture fluids were prepared by centrifugation at room temperature for 10 minutes at 200 xg and analyzed for inhibition of IL-6 activity in the B9 cell assay.

FIG. 2: Effects of IL-6 inhibitor on Proliferation of U373 Cells.

HL-60 cells ($1\times10^6$ cells/mL) were treated with PMA (10 ng/mL) for 24 hours. Cells were washed, resuspended in RPMI-2 and incubated for 3 days. Culture fluids were prepared by centrifugation and analyzed in the U373 assay with or without IL-1α. Anti-IL-1 (1 μg/well) was used for comparison.

FIGS. 3(A) and 3(B): Optimization of Cell Density and PMA Concentration.

HL-60 cultures were established at the indicated cell density and incubated for 24 hours with the indicated concentration of PMA in RPMI-2. Cells were harvested, washed and resuspended at the initial cell density. After 24 hours, cell-free tissue culture fluids were analyzed in the B9 assay in the presence of IL-6. Effect of cell density FIG. 3(A) and PMA concentration FIG. 3(B) on expression of inhibitor are shown.

FIG. 4: Superose 12® HR 10/30 Chromatography of HL-60 Supernatant.

TCF was concentrated approximately 17 fold with a YM3 membrane and diafiltered into 50 mM Sodium Phosphate pH 7.0 (starting buffer). 0.5 mL of concentrate was applied to the column. The column buffer was 10 mMTris, 150 mM NaCl, pH 7.8. The column flow rate was 0.5 mL/min and 1 mL fractions were collected. Fractions were directly tested for inhibitor activity with the B9 assay.

FIG. 5: Mono Q® Chromatography of HL-60 Supernatant.

TCF was concentrated approximately 17 fold with a YM3 membrane and diafiltered into starting buffer. The column was equilibrated with 20 mM Tris pH 7.5. The concentrated TCF was diluted 1:2 with the Tris buffer and 0.5 mL was loaded onto the column. Protein was eluted in a linear gradient with the final buffer containing 20 mM Tris, 1M NaCl pH 7.5. 0.5 mL fractions were collected into BSA-containing tubes. To assay for inhibitor activity, 0.4 mL of a fraction was concentrated 4–8 fold and diafiltered with RPMI-1640.

FIG. 6: Blue Sepharose® Chromatography of HL-60 Supernatant.

TCF was concentrated with a YM10 membrane approximately 87 fold and diafiltered into starting buffer. The concentrated TCF was loaded onto a 50 mL column and the column was washed with starting buffer. A linear gradient of 0 to 1M NaCl in starting buffer was then applied followed by elution with 50% ethylene glycol in 50 mM Sodium Phosphate, 4M NaCl pH 7.0. 10 mL fractions were collected. For use in the B9 assay, samples of the collected fractions were concentrated 4–8 fold and diafiltered into RPMI-1640.

FIGS. 7(A) and 7(B): Reverse Phase Chromatography of HL-60 Inhibitory Activity Eluted from Blue Sepharose® Chromatography.

Fractions from Blue Sepharose® chromatography containing inhibitor activity were combined into two pools, the first eluting FIG. 7(A) at approximately 900mMNaCl in the linear gradient and the second FIG. 7(B) eluting with 50% ethylene glycol, 4M NaCl. The pools were concentrated approximately 100 fold and applied separately to a 2 mL ProRPC® reverse phase column equilibrated with 0.1% (v/v) trifluoroacetic acid (TFA) in water. The column was washed with the starting buffer and eluted with a 20% (v/v) to 80% (v/v) linear gradient of HPLC grade acetonitrile in 0.1% (v/v) TFA. Fractions (0.3 mL) were collected, evaporated to dryness, and resuspended in 0.1 mL $H_2O$ for analysis in the B9 assay.

FIG. 8: Reverse Phase Chromatography of HL-60 Inhibitory Activity Isolated by Reverse Phase Chromatography.

Active fractions from the reverse phase chromatography of Blue Sepharose® pools A and B were combined and rechromatographed on the 2 mL ProRPC® column using a 20 to 80% (v/v) acetonitrile gradient in 0.1% TFA. Fractions were analyzed for IL-6 inhibitor activity as described in FIG. 7.

FIG. 9: Heat Treatment of HL-60 Inhibitor.

The following samples were heated for 15 min at 100° C. and then tested for inhibitory activity in the B9 assay. (1)Blue Sepharose® Peak 2: undiluted, (2)Blue Sepharose® Peak 2: 1:10, (3)Blue Sepharose® Peak 2: 1:100, (4)Blue Sepharose® Peak 2: 1:1000, (5)Anti IL-6, 5.0 µg/mL, (6)Anti-IL-6, 0.5 µg/mL, (7)Anti-IL-6, 50 ng/mL, (8)Anti-IL-6, 5 ng/mL, (9)RPMI-2: Undiluted, (10)RPMI-2: 1:10, (11)RPMI-2: 1:100, (12)RPMI-2: 1:1000.

FIG. 10: Trypsin Digest of HL-60 Inhibitor.

Using a 10 kD molecular weight cut-off filter, 500 µL of a Blue Sepharose® pool containing IL-6 inhibitor activity, was diafiltered into 0.1M Ammonium Bicarbonate pH 8.0 (digestion buffer). Samples (250 µL/sample) were added to separate pellets of immobilized trypsin previously washed in digestion buffer and incubated at 37° C. for 3.5 hours. Trypsin digests were recovered by centrifugation, sterile filtered, and compared against untreated samples in the B9 assay.

FIG. 11: Acid Treatment of HL-60 Inhibitor.

An Blue Sepharose® pool containing IL-6 inhibitor was diluted 1:2 in either 0.1% trifluoroacetic acid/100% acetonitrile, pH≦2 or sterile water. After evaporation to dryness, the samples were reconstituted in 100 µL RPMI, sterile filtered, and analyzed by the B9 assay.

FIG. 12: Effect of Cycloheximide on Synthesis of HL-60 Inhibitor.

HL-60 cells ($10^6$/mL) were treated with PMA (10 ng/mL). After 24 hours adherent cells were washed in RPMI-2 and non-adherent cells were removed. Duplicate cultures were then incubated in either RPMI-2 or RPMI-2 containing 100 µg/mL cycloheximide. After an additional 24 hours, TCF was removed and the cells were washed to remove cycloheximide. Cells were incubated in RPMI-2 for 2 more days at which time TCF was harvested for analysis of inhibitory activity in the B9 assay. All TCF samples were diafiltered prior to assay to ensure removal of cycloheximide.

DETAILED DESCRIPTION OF THE INVENTION

Reagents

Phorbol Myristate Acetate (PMA), Phorbol dibutyrate (PDBu), A23187, all-trans-retinoic acid (RA), and dimethyl sulfoxide (DMSO) were purchased from Sigma Chemical Co. Stock solutions of PMA, PDBu, A23187, and RA were stored in ethanol at −20° C. All reagents were protected from light and diluted into the appropriate medium immediately prior to use. Recombinant human IL-6 was purchased from Genzyme. Anti-IL-6, anti-IL-1α, anti-IL-1β, and recombinant human IL-1α were purchased from R&D Systems.

Cell Culture

Two HL-60 cell lines (ATCC #CCL-240) were used to generate the inhibitory activity. The first cell line secreted high levels of IL-6 and the second secreted 20 pg/mL or less of IL-6. The cell lines were maintained in RPMI-1640 (Gibco) supplemented with 10% heat inactivated FBS (Hyclone) (RPMI-10). Cells were washed in $Ca^{2+}$ and $Mg^{2+}$ free Dulbecco's phosphate buffered saline (DPBS-CMF, Gibco) and resuspended in RPMI-1640 containing the appropriate inducing agent(s). Tissue culture fluids (TCF) were harvested and IL-6 inhibitor activity was determined using the B9 assay.

Initial experiments to determine optimal inducer and cell concentrations were performed with the IL-6 secreting cell line. Subsequent experiments demonstrated that the non-secreting HL-60 line produced an IL-6 inhibitor after phorbol diester (e.g. PMA, PDBu, etc.) stimulation. By gel filtration, the inhibitor synthesized by the IL-6 non-secretor had the same molecular weight as the inhibitor synthesized by the IL-6 secretor. To avoid aberrant results due to the presence of IL-6, characterization and purification studies were done using the non-secreting cell line which is available from the ATCC.

IL-6 Dependent B9 Assay

The B9 murine hybridoma cell line (gift from P. Scuderi, Miles Research Center; West Haven, CN) was maintained in RPMI-10 supplemented with at least 1 unit/mL IL-6. For use in the assay, the cells were seeded at 5×10⁴ cells/mL in RPMI with 5% FBS (RPMI-5) in 96-well plates (Corning) at 100 μL/well. Volumes of 20 μL (crude TCF) or 10 μL (column fractions) from samples to be tested were added. One-half of the wells received 100 μL of IL-6 at 2 units/mL in RPMI-5 and the other half received 100 μL of RPMI-5. Anti-IL-6 was added to control wells at 0.5–1 μg/well to ensure that IL-6 specific effects were being measured. After a 3–4 day incubation period, cell proliferation was measured by either ³H-Thymidine (³H-Tdr, DuPont-NEN) incorporation or by conversion of MTS tetrazolium (Promega) into an aqueous soluble formazan. For ³H-Tdr incorporation, the cells were labelled with 0.5 μCi/well ³H-Tdr for 5 hours, harvested onto filters using the Tomtec Autotrap and ³H incorporation was determined using a 1205 BS Betaplate (LKB-Wallac). For non-radioactive detection of cell proliferation, the Cell Titer 96 AQ Non-radioactive Cell Proliferation Assay (Promega) was used. Samples were assayed in triplicate and percent inhibition was calculated from the mean values in the following manner:

$$\frac{[(CPM_{(RPMI+IL-6)} - CPM_{(RPMI-IL-6)}) - (CPM_{(test+IL-6)} - CPM_{(RPMI-IL-6)}) \times 100]}{[(CPM_{(RPM+IL-6)} - CPM_{(RPMI-IL-6)})]}$$

To determine percent inhibition in the non-radioactive assay, O.D. values were used instead of CPM in the above equation.

IL-1 Dependent U373 Assay

The growth promoting effects of IL-1 on the U373 (human astrocytoma/glioblastoma) cell line have been reported by others (Lachman et al., *J. Immunol.*, 138(9):2913-29-6 (1987)). For use in the assay, U373-MG cells (ATCC #HTB 17) were grown to confluence in RPMI-10. One day prior to testing, cells were treated with trypsin and 1×10⁴ cells/well were seeded into 96-well plates in RPMI containing 1% FBS (RPMI-1). Test samples, 20 μL of tissue culture fluid (TCF), were then added with or without 5 units/mL of IL-1α in a total volume of 200 μL/well. RPMI-2 was added in the appropriate volume to serve as a negative control. Cells were cultured for 2 days and 0.5 μCi/well of ³H-Tdr was added for the terminal 5 hours. Cells were harvested and ³H incorporation was determined.

Column Chromatography

PMA-induced HL-60 culture supernatants were diafiltered into the indicated buffer and concentrated by ultrafiltration with a YM10 or YM3 membrane (Amicon). The concentrated supernatants were applied to the chromatography resins and eluted as described in the figures. To assay for IL-6 inhibitor activity, the fractions were filtered through a 0.22 μm filter and, if the elution buffer was incompatible with the B9 assay, diafiltered with RPMI-1640. All resins were purchased from Pharmacia unless otherwise noted.

SDS-PAGE

Samples to be electrophoresed were diluted 1:2 with non-reducing SDS-PAGE buffer and boiled 5–10 min at 100° C. 20 μL of the diluted samples were loaded onto 10–20% gradient SDS-PAGE gels (BioRad) and electrophoresed at 200 V for approximately 45 min. The gels were stained with Coomassie Blue R-250 or silver stained.

Example 1

The effects of various compounds known to modulate the differentiation of HL-60 cells in vitro are summarized in FIG. 1. 0.5–2×10⁶ HL-60 cells per mL RPMI-1640 were treated with 10 ng/mL PMA or 130 ng/mL PDBu, both of which are known to induce monocytic differentiation. After 24 hours, the cells became adherent, vacuolated and ceased to grow. The cells were transferred into RPMI-2 and 3 days later an IL-6 inhibitor as determined with the B9 assay was found in the culture fluids of the cells treated with either PMA or PDBu, but not in the culture fluids of cells treated with DMSO or RA, which induce granulocytic differentiation. In some cell lines calcium ionophores and phorbol esters synergistically elicit cellular activation. However, we found that co-stimulation with PMA and a calcium ionophore (A23187) did not increase the level of inhibitor over that induced by PMA alone. A23187 alone did not generate a detectable inhibitor.

The IL-6 inhibitor was detected in culture fluids within 24 hours of PMA addition and secretion continued for an additional 48 hours after removal of the inducing agent. Despite the fact that PMA alone can stimulate B9 cell growth and the first harvest of HL-60 culture fluids potentially contained 10 ng/mL of residual PMA, inhibitory activity was still observed in the crude supernatant of this harvest.

Example 2

In addition to inhibiting the IL-6 stimulated proliferation of B9 cells, the HL-60-derived inhibitor suppressed the endogenous (IL-6 independent) growth of B9 cells. Anti-IL-6 only affected IL-6 stimulated proliferation. To rule out the possibility that the HL-60-derived activity was an inhibitor of thymidine incorporation or a non-specific inhibitor of cell proliferation, the effect on U373 cells was analyzed. Proliferation of U373 cells is stimulated by IL-1 but not by IL-6. See FIG. 2. 1×10⁶ HL-60 cells/mL were treated with 10 ng/mL PMA for 24 hours. The cells were transferred into RPMI-2 and incubated for 3 days further. The supernatant was collected and assayed in the U373 assay. No inhibitor of IL-1 stimulated proliferation or non-specific inhibitor of cell growth was detected in the culture fluids of PMA induced HL-60 cells as determined by the U373 assay. In fact, HL-60 culture fluids were found to stimulate proliferation of U373 cells presumably due to the presence of IL-1 in the supernatant. Control experiments using anti-IL-1 gave the expected results. In addition, the HL-60 inhibitor did not inhibit IL-2 dependent or non-specific proliferation of CTLL cells.

Results

The initial studies were expanded to determine the best conditions for induction of inhibitor. Optimal inhibitor production was observed using HL-60 cell densities ranging from 0.5 to 2.0×10⁶ cells/mL and PMA concentrations from 1–10 ng/mL (see FIG. 3).

Characterization of the Inhibitor

Column Chromatography: The IL-6 non-secreting HL-60 cell line was used to further characterize the inhibitor as well as fractionate the inhibitor activity from contaminating proteins. Size exclusion, anion exchange, Blue Sepharose®, and reverse phase chromatography were utilized. In order to simplify large scale purification, cells were induced in serum-free RPMI-1640.

To approximately determine the molecular weight of the inhibitor, the TCF was ultrafiltered through a 30 kD membrane. Activity was found in the filtrate after concentration with a 10 kD membrane indicating that the molecular weight of the inhibitor is less than 30 kD but greater than 10 kD.

To further characterize the inhibitor, concentrated and diafiltered TCF was chromatographed on a Superose 12® gel filtration column. See FIG. 4. The activity eluted at a position corresponding approximately to 20 kD. IL-6 was determined by ELISA (R&D Systems).

HL-60 TCF was concentrated and applied to a Mono Q® anion exchange column. See FIG. 5. The fractions from the Mono Q® column were assayed for inhibitor activity and activity was found to elute at 175 mMNaCl. From DEAE-Sephacel®, inhibitor activity was found to elute at 150 mM NaCl.

Because Blue Sepharose® had been used previously to isolate cytokines, TCF containing the IL-6 inhibitor was chromatographed on this resin. See FIG. 6. Under the conditions used, the bulk of the protein in the TCF did not bind to the column. The inhibitor activity eluted in a broad peak at approximately 900 mMNaCl (Pool A) or in the subsequent 50% ethylene glycol/4M NaCl (Pool B). By SDS-PAGE, the inhibitory peak fractions from Blue Sepharose® contained multiple proteins.

C1/C8 reverse phase chromatography (ProRPC®) was used to further purify the inhibitor. See FIG. 7. IL-6 inhibitory activity from either Blue Sepharose® pool A (FIG. 7A) or pool B (FIG. 7B) was found to elute at approximately 40% acetonitrile. The active fractions from these runs were combined and rechromatographed on ProRPC® using a shallower gradient to improve resolution (FIG. 8). Inhibitory activity eluted at approximately 32% acetonitrile. SDS-PAGE analysis (10 to 20% gradient gel) revealed the presence of multiple protein bands. Thus, although significant purification of the inhibitor from TCF has been achieved, the inhibitor has not yet been purified to homogeneity.

Characterization:

A partially purified pool of inhibitor eluted from Blue Sepharose® was heated at 100° C. for 15 minutes without any significant loss of inhibitory activity in contrast to what was observed with anti-IL-6 (see FIG. 9). Treatment of the Blue Sepharose® pool with immobilized trypsin reduced inhibitor activity 64 fold (see FIG. 10). Treatment of the TCF with 0.1% trifluoroacetic acid in acetonitrile at pH≦2 resulted in a 3 fold loss of activity (see FIG. 11). Incubation of HL-60 cells after PMA stimulation with cycloheximide, a known protein synthesis inhibitor, resulted in the complete suppression of inhibitor activity in the B9 assay (see FIG. 12). The results of the above experiments strongly suggest that the inhibition seen is the result of a protein present in the HL-60 TCF.

Discussion

An inhibitor of IL-6 stimulated proliferation of B9 hybridoma cells was detected in the culture fluids of HL-60 cells induced to differentiate toward the macrophage lineage. Phorbol myristate acetate (PMA) and the non-lipophilic diester phorbol dibutyrate (PDBu) were effective as inducers of the inhibitory activity. Inducer concentration and cell density were found to be critical parameters for optimization of inhibitor expression, e.g. 1–10 ng/mL PMA and 0.5–2.0× $10^6$ cells/mL. Differentiation of HL-60 cells along the granulocytic pathway with retinoic acid (RA) and dimethyl sulfoxide (DMSO) did not induce detectable levels of the inhibitor. Exposure of cells to the calcium ionophore A23187 with or without PMA or to combinations of RA and PMA, conditions which have been reported to enhance activation of monocytic cell lines, had no significant effect on expression of inhibitor.

The HL-60 derived activity had no inhibitory effect on the IL-1 dependent or spontaneous rate of proliferation of U373 cells. These data suggest that the activity is not an inhibitor of thymidine uptake or IL-1 action, or a non-specific inhibitor of cell proliferation. Nevertheless, the HL-60 inhibitor suppressed the spontaneous rate of B9 cell proliferation observed in the absence of added IL-6, in addition to the stimulated rate induced by exposure of B9 cells to PMA. Although anti-IL-6 had no effect on the spontaneous proliferation of B9 cells, endogenous synthesis of the cytokine may provide an autocrine growth effect and such autocrine effects may be refractory to inhibition by antibodies. The mechanism by which PMA stimulates B9 cell proliferation is unknown, but could also depend upon endogenous synthesis of IL-6, since B9 cells respond to no other known cytokines. We tentatively conclude that the HL-60 derived activity is likely a specific inhibitor of both added and endogenous IL-6. It is interesting to note that the inhibitory activity can be found in HL-60 supernatants that contain rather high concentrations of IL-6. This observation suggests a mechanism distinct from receptor antagonism, which would be consistent with the differential effects of anti-IL-6 and the HL-60 inhibitor on spontaneous and PMA-induced B9 cell proliferation.

To the best of our knowledge, no naturally occurring IL-6 inhibitors have been described to date. As used herein, naturally occurring human inhibitor means a non-genetically engineered compound derived from human cells that inhibits the actions of IL-6. Soluble IL-6 receptors have been reported, but have been found to stimulate rather than inhibit IL-6 activity. This is a unique observation, since other soluble cytokine receptors are known to be antagonists. The agonist activity is most likely due to the configuration of the IL-6 receptor; a primarily extracellular 80 kD subunit which binds to IL-6 with low affinity and gp 130, which after binding to the IL-6/80 kD complex, increases the affinity of the 80 kD receptor for IL-6 and causes signal transduction. Presumably a soluble receptor-IL-6 complex is recognized and bound by gp130 and the IL-6 signal is transduced.

Overexpression of IL-6 has been documented in autoimmune diseases such as systemic lupus erythematosus and rheumatoid arthritis and the cytokine is known to be a growth factor for neoplastic plasma cells. Although effects of IL-6 antagonists have not been reported for autoimmune diseases, a role for the cytokine in pathogenesis has been proposed on the basis of available data. A short term clinical response was noted using a murine monoclonal antibody in patients with plasma cell leukemia, suggesting that effective blockade of IL-6 function would be a beneficial adjunct to current therapy.

The above examples are intended to illustrate the invention and it is thought variations will occur to those skilled in the art. Accordingly, it is intended that the scope of the invention should be limited only by the following claims.

We claim:

1. A purified Interleukin 6 inhibitor characterized by:

A being obtainable from the HL-60 cell line,

B having a molecular weight between 10,000 daltons and 30,000 daltons as determined by gel filtration chromatography, C being capable of suppressing Interleukin 6 dependent proliferation of Interleukin 6 dependent cell lines, D being bindable and elutible from Cibacron Blue linked resins, E being bindable and elutible from anion exchange resins and F being bindable and elutible from reverse phase resins.

2. The inhibitor preparation of claim 1 wherein the inhibitor elutes from Cibacron Blue resins at NaCl concentrations greater than about 800 mM and pH between about 6.5 to 7.5.

3. The inhibitor preparation of claim 1 wherein the inhibitor elutes from anion exchange resins at NaCl concentrations greater than about 140 mM and pH between about 7.0 to 8.0.

4. The inhibitor preparation of claim 1 wherein the inhibitor elutes from C1/C8 reverse phase resins at acetonitrile concentrations from about 30–50%.

5. The inhibitor preparation of claim 1 wherein the suppression of proliferation is reduced greater than 50 fold by digestion with trypsin.

6. The inhibitor preparation of claim 1 wherein the suppression of proliferation is abrogated by incubation of said HL-60 cells with cycloheximide.

7. The inhibitor preparation of claim 1 wherein the suppression of proliferation is unaffected by heating at 100° C. for 15 minutes.

8. The inhibitor preparation of claim 1 wherein the suppression of proliferation is reduced greater than or equal to 2 fold by treatment with acid.

9. The inhibitor preparation of claim 1 wherein the Interleukin 6 dependent cell line is B9.

10. The inhibitor preparation of claim 1 wherein the HL-60 cells are treated with phorbol diesters.

11. A method of preparing the Interleukin 6 inhibitor of claim 1 comprising the step of contacting HL-60 cells with phorbol esters under conditions sufficient to induce said Interleukin 6 inhibitor production.

* * * * *